United States Patent [19]

Morrone

[11] Patent Number: 4,670,480

[45] Date of Patent: Jun. 2, 1987

[54] DENTAL PROSTHESIS COMPOSITION

[76] Inventor: Rudolph D. Morrone, 2120 Chapel Ave., Cherry Hill, N.J. 08002

[21] Appl. No.: 766,246

[22] Filed: Aug. 16, 1985

[51] Int. Cl.[4] .......................... A61F 2/00; C08F 8/06
[52] U.S. Cl. .................................. 523/115; 523/116; 525/387
[58] Field of Search ................ 523/116, 115; 525/193, 525/309, 227, 383, 387; 526/208

[56] References Cited

U.S. PATENT DOCUMENTS

| | | | |
|---|---|---|---|
| 4,110,184 | 8/1978 | Dart et al. | 523/116 |
| 4,282,140 | 8/1981 | Bousquet et al. | 525/193 |
| 4,369,262 | 1/1983 | Walkowiak et al. | 525/309 |
| 4,459,193 | 7/1984 | Ratcliffe | 526/208 |
| 4,529,777 | 7/1985 | Daidone | 525/227 |

*Primary Examiner*—Theodore Morris
*Attorney, Agent, or Firm*—Thomas A. Lennox

[57] ABSTRACT

A dental prosthesis composition which may be used for crowns and the preparation of dentures offering improved physical properties together with heat formability at temperatures that can be withstood in the mouth. The composition includes an acrylic polymer, an alkyl methacrylate monomer and a catalysis to cure the composition at room temperature with the addition of one to thirty parts per 100 parts of the liquid by weight of a dialkyl ketone, such as a dimethyl ketone.

11 Claims, No Drawings

DENTAL PROSTHESIS COMPOSITION

BACKGROUND OF THE INVENTION

This invention involves a dental prosthesis composition and more particularly is an acrylic polymeric composition capable of polymerization in any desired shape.

The composition of the present invention may be used to prepare full and partial dentures, restoration of carious teeth, as a pit and fissure sealant, as an impression material, as a peripheral seal and fast setting tray material, crown and bridge temporary restoration, a repair composition and other similar applications. Popular and typical polymeric resin compositions for the above applications are those based upon alkyl methacrylate polymers and copolymers and in particular polymers and copolymers of methyl methacrylate. Typical comonomers include butyl methacrylate, ethyl acrylate, and dimethacrylates such as ethylene glycol dimethacrylate, aromatic dimethacrylates such bis-phenol glycidyl methacrylate, urethane diacrylate and other comonomers. A common composition utilizes a portion of difunctional monomer so that cross-linking of the polymerized system results. A typical prosthesis composition includes an acrylic polymeric powder in the form of small beads which is mixed by the dentist or prosthesis preparer with an acrylic monomer composition to form a paste. If the polymerization of the monomer is to take place at elevated temperatures, a peroxide such as benzoyl peroxide, a white powder, is included mixed with the polymer powder. If the composition is to be cured at room temperature, generally described as "cold cure", an accelerator/initiator such as an aromatic tertiary amine is premixed with the monomer such that when the monomer and the polymer are mixed together, the accelerator reduces the half-life of the peroxide and causes polymerization or "cure".

Compositions of dental materials, their preparation, and physical properties are described in great detail in *OUTLINE OF DENTAL MATERIALS AND THEIR SELECTION* by William J. O'Brien, Ph.D and Gunnar Ryge, D.D.S. and M.S., 1978. W. B. Saunders Company, West Washington Square, Philadelphia, Pa. 19105, Library of Congress ISBN 0-7216-6896-8 and Air Force Manual *DENTAL LABORATORY TECHNOLOGY* Jan. 22, 1975 supplied by Department of the Air Force, available from Superintendent of Documents, U.S. Government Printing Office, Washington, D.C. 20402, Catalog NO. D 301.7:162-6 and later editions, all incorporated herein by reference.

It is recognized that some of the physical properties of the cold cured acrylic polymer prosthesis compositions are inferior to the physical properties of the oven cured acrylic resins. While it is well recognized that the glass transition temperature, that is the softening temperature, for the "pour-type", cold cured acrylic resins has lower mechanical softening temperatures than the heat cured acrylic resins. In addition, other, more subtle characteristics of the cold cured resin are inferior such as the wetability accuracy, warping, generally due to shrinkage and surface hardness using some tests. Wetability may be described in more technical terms as the contact angle between the liquid and the solid cured resin surface or the surface tension between the liquid surface and the resin surface. The practical advantage of being more hydroscopic is appearance and improved adhesion between the denture and the mouth to keep the plate in place. A number of prosthetic methods and devices have been described in U.S. Patents and all of the techniques and devices may be utilized using the present invention. These patents include U.S. Pat. No. 2,036,715 to H. D. Morgan, U.S. Pat. No. 3,083,459 to M. McMurry et al, U.S. Pat. No. 3,307,260 to Robert H. Allen, U.S. Pat. No. 2,101,431 to Groff, U.S. Pat. No. 3,659,344 to Gavazzi, U.S. Pat. No. 4,017,971 to Hazar and U.S. Pat. No. 4,044,762 to Jacobs all the patents being incorporated herein by reference.

The needs described above and the objects herein below are not satisfied by the compositions or devices of the above patents.

SUMMARY OF THE INVENTION

The invention is a dental prosthesis composition including a polymerizable composition including an acyrlic polymer powder, an alkyl methacrylate monomer and a catalysis system to induce polymerization of the monomer. Added to that composition is one to thirty parts of a dialkyl ketone per hundred parts of the weight of the monomer and dialky ketone mixture. It is preferred that the composition be four to eighteen parts dialkyl ketone per hundred parts of a liquid mixture and more preferably contain five to fourteen parts per hundred parts of the liquid.

A preferred catalysis means includes a peroxide such as benzoyl peroxide and an accelerator such as dialkyl p-toluidine to cause and promote polymerization at room temperature, that being the "pour-type" or cold cure version. It is preferred that the dialkyl ketone have alkyl groups having one to four carbon atoms and dimethyl ketone is particularly preferred. It is preferred that the alkyl methacrylate monomer have alkyl groups having one to four carbons atoms and methyl methacrylate is particularly preferred. The monomer mix generally contains a cross-linking monomer. The polymer is preferably based on methyl methacrylate but may have comonomers such as ethyl acrylate to affect the physical characteristics.

This composition, particularly when cured at room temperature using the "cold cure" technique, provides a heat deformable composition which may be heated prior to insertion in the mouth and then molded to the shape of the mouth to form a rough fitting an impression or a denture base plate. With this composition, a temporary or inexpensive denture can be produced using a cured sheet of the composition which when roughly shaped in the mouth and then filled with the composition of this invention and cured in the mouth. After cure, the denture conforms directly to the mouth and the gums.

It is an object of this invention to provide a new dental prosthesis composition offering an improved and different combination of physical properties.

It is another object of this invention to provide a cold cure acrylic composition that offers important physical properties approaching or improved over the hot cure system.

It is a further object of the present invention to provide a dental prosthesis composition which is heat deformable and will conform to the contour of the mouth upon cooling.

It is a particular object of the present invention to provide a dental prosthesis composition with improved "wetability" and strength approaching that of hot cured resins.

It is an object of the present invention to provide a method by which a temporary denture can be produced to conform and reproduce the shape of the gum.

It is a further object of the present invention to orovide a quick and inexpensive method of producing a denture.

It is a particular object of the present invention to provide a composition which may be used to take a gum impression and then realign and fit that impression with a stock denture and conform the denture exactly to the patient's gum shape.

DESCRIPTION OF PREFERRED EMBODIMENTS

A composition is prepared based on a impact resistant denture based material marketed under the trade designation IMPACT 76 by Kerr Sybrone, 28200 Wick Rd., Romulus, Mich., 48174. An alternative material is CAULK ® repair material supplied by Dentsply/York Division, Dentsply International Inc., York, Pa. 17405. Three parts of the acrylic polymer powder is mixed with one part of the monomer liquid. Before mixing, ten per cent by volume of the monomer is replace with dimethyl ketone. The resin is mixed and cured at room temperature into a flat denture base plate. After hardening, the plate is heated to 180° F. which permits the material to soften sufficiently that it may be molded to the patient's mouth. After the denture base plate has cooled to mouth temperature, the plate remains rigid and formed to the shape of the patient's gum. A set of premolded teeth, sufficient to replace those lost by the patient are temporarily fixed with wax to the base plate and again fit into the patient's mouth to check spacing and articulation. If satisfactorily placed, the teeth are attached with a small quantity of the composition prepared above and then removed from the mouth. Using a larger quantity of the acrylic resin composition, all of the teeth are fixed to the base plate in a permanent fashion. Because the denture base plate is not able to conform to every depression on the patient's mouth, there remains voids between the base plate and the mouth. A quantity of the acrylic composition is prepared and smeared on the surface of the base plate that contacts the gum and replaced directly into the mouth. The plate is kept in the biting position while the resin cures between the plate and the gum. After curing and polishing, an exact fitting denture is produced. The addition of the dimethyl ketone increases the speed of cure and reduces the set-up time so that prompt action by the dentist is required. Using this system, the dentures are essentially articulated in the mouth to make sure that there is proper fit and engagement of the teeth. There is little or no discomfort to the patient and a temporary denture is quickly and inexpensively produced. This composition may also be used to take an impression of the patient's mouth, upper and lower gums, pouring models, taking a bite and using the bite to articulate models on an articulator.

To demonstrate the physical properties of the compositions of the present invention 23 grams of a methyl methacrylate polymer in the form of beads having a diameter in the range of 50 to 250 millimicrons is placed in a glass beaker. Benyzol peroxide is added to the powder and mixed thoroughly. A monomer mixture is prepared of 8.5 grams methyl methacrylate monomer, 0.5 gram ethylene glycol dimethacrylate cross-linking monomer and an aromatic tertiary amine. The powder and monomer mixtures are blended and masticated together to form a paste which is then formed into a plate spread on a glass surface which has been sprayed a silicone release agent, and allowed to cure at room temperature.

Composition B. The composition and the method of preparation is repeated for Composition A except that 0.1 gram dimethyl ketone is added to 8.9 grams of the monomer mixture, mixed with the polymer and cured in the same fashion. This is about 0.1 ml. dimethyl ketone in 9.9 ml. of monomer or about 1.1 weight per cent of total liquid mix.

Composition C. The composition and the method of preparation is repeated as in Composition A except that 0.4 gram dimethyl ketone is added to 8.5 grams of the monomer mixture before mixing with the polymer powder. This is about 0.5 ml. in 9.5 ml. monomer for 4.5 wgt. per cent.

Composition D. Composition A preparation is repeated except that 0.8 gram dimethyl ketone is added to 8.0 grams of the monomer mixture before mixing with the polymer. This is about 1.0 ml. in 9.0 ml. monomer for 9.1 wgt. per cent.

Composition E. Composition A is repeated except that 1.2 grams dimethyl ketone is added to 7.6 grams of the monomer mixture prior to mixing with polymer. This is about 1.5 ml. in 8.5 ml. monomer for 13.6 wgt. percent.

Composition F. Composition A is repeated except that 1.6 grams dimethyl ketone is added to 7.1 grams of the monomer mixture prior to mixing with the polymer. This is about 2.0 ml. in 8.0 ml. monomer for 18.4 wgt. per cent.

Composition G. Composition A is repeated except that 2.4 grams dimethyl ketone is added to 0.2 grams of the monomer mixture prior to mixing with the polymer. This is about 3.0 ml. in 7.0 ml. monomer for 27.9 wgt. per cent.

Composition H. Composition D is repeated except that dibutyl ketone is substituted for the dimethyl ketone.

Composition I. Composition C is repeated except that the monomer mix is 4.5 grams methyl methacrylate and 4.5 grams ethyl methacrylate.

As the concentration of dialkyl ketone is reduced below 5 parts per hundred parts liquid mixture monomer and approaches one part dialkyl ketone per hundred parts liquid mixture, the effect on physical properties is reduced and only slight improvement is observed. As the composition includes increasing amounts of dialkyl ketone above 20 parts and above 30 parts per hundred parts liquid mixture, the effect on physical properties is noticeably adverse in relation to the end use. Addition of the dialkyl ketone quickly solubilizes and appears to melt the polymer and speeds the polymerization of the monomer. The cured polymers have improved accuracy, definition and reproduction of the shape with improved wetability and hardness approaching that of the heat cured resins.

The compositions have improved "wetablility". That term in describing the improvement enjoyed by compositions of the present invention relates to a variety of physical characteristics observed in relation to the use in dental prosthesis and relates to any and all of the various characteristics described in Chapter 4 of *OUTLINE OF DENTAL MATERIALS AND THEIR SELECTION*, referred to herein above. The term "acrylic polymer" or "methyl methacrylate polymer" refers to not only the homopolymer but various copolymers and modified polymers including but not limited to homopolymers of methyl methacrylate, ethyl methacrylate, butyl methacrylate, methyl acrylate, ethyl acrylate, copolymers of methyl methacylate and lower alkyl esters of acrylic and methacrylic acids, and copolymers of methyl methacrylate with minor amounts of one or more of the following: lauryl methacrylate, isobornyl methacrylate, acrylamide, hydroxyethyl methacrylate, styrene, 2-ethylhexyl acrylate, acrylonitrile, methacrylic acid, methacrylamide, methyol acrylamide and cetyl stearyl methacrylate, and the like.

The term "alkyl methacrylate monomer mix" refers not only to alkyl methacrylate monomers but to various mixtures of monomers including but not limited to methyl methacrylate, ethyl methacrylate, butyl methacrylate, methyl acrylate, ethyl acrylate, lauryl methacrylate, isobornyl methacrylate, cross-linking monomers including but not limited to diallyl pthalate, bis-phenol glycydyl methacrylate, alkylene glycol dimethacrylates, such as ethylene glycol dimethacrylate, and other monomers used in dental material compositions.

The use of the dialkyl ketone in the composition may be used with bis-phenol glycidyl methacrylate prepolymers. The terms acrylic polymer powder and alkyl methacrylate monomer are intended to include such prepolymers. Those prepolymers are typically used for restoration compositions.

While this invention has been described with reference to the specific embodiments disclosed herein, it is not confined to the details set forth and the patent is intended to include modifications and changes which may come within and extend from the following claims.

I claim:
1. A dental prosthesis composition comprising:
    (a) polymerizable composition comprising an acrylic polymer, an alkyl methacrylate monomer mix and a catalysis means to induce polymerization of the monomer, and
    (b) one to twenty-eight parts dialkyl ketone per parts by weight of the monomer and dialkyl ketone mixture.
2. The composition of claim 1 wherein the catalysis means comprises a peroxide and accelerator means to cause and promote polymerization at room temperature.
3. The composition of claim 1 wherein the dialkyl ketone has alkyl groups having one to four carbon atoms.
4. The composition of claim 1 wherein the dialkyl ketone is dimethyl ketone.
5. The composition of claim 1 wherein the alkyl methacrylate monomer mix comprises an alkyl methacrylate has alkyl groups having one to four carbon atoms.
6. The composition of claim 5 wherein the alkyl methacrylate is methyl methacrylate.
7. The composition of claim 1 wherein the acrylic polymer is based on methyl methacrylate.
8. The composition of claim 1 wherein the weight of the dialkyl ketone is four parts to eighteen parts per hundred parts weight of the monomer and dialkyl ketone mixture.
9. The composition of claim 1, wherein the weight of the dialkyl ketone is five parts to fourteen parts per hundred arts by weight of the monomer and dialkyl ketone mixture.
10. The composition of claim 1, wherein the acrylic polymer is in the form of bead powder.
11. A dental prosthesis composition comprising:
    (a) a polymerizable composition comprising a methyl methacrylate polymer, an alkyl methacrylate monomer and a catalysis means comprising a peroxide and accelerator to cause and promote polymerization of the monomer at room temperature, and
    (b) five parts to fourteen parts by weight of dimethyl ketone per one hundred parts of the alkyl methacrylate monomer and dialkyl ketone mixture.

* * * * *